United States Patent [19]

Hemker et al.

[11] Patent Number: 5,192,689
[45] Date of Patent: Mar. 9, 1993

[54] METHOD FOR DETERMINING THE ENDOGENOUS THROMBIN POTENTIAL OF PLASMA AND BLOOD

[76] Inventors: Hendrik C. Hemker, Tongersestraat 41, 6211 LM Maastricht; Suzette L. Beguin, Akerstraat 12b, 6221CL Maastricht, both of Netherlands

[21] Appl. No.: 588,924

[22] Filed: Sep. 27, 1990

[30] Foreign Application Priority Data

Sep. 27, 1989 [NL] Netherlands ............... 8902406

[51] Int. Cl.$^5$ ............................................. G01N 33/86
[52] U.S. Cl. ......................................... 436/69; 435/13
[58] Field of Search .................. 422/61; 436/34, 69; 435/13

[56] References Cited

U.S. PATENT DOCUMENTS

| | | | |
|---|---|---|---|
| 4,061,625 | 12/1977 | Af Ekenstam et al. | 435/13 X |
| 4,169,015 | 9/1979 | Af Ekenstam et al. | 435/13 |
| 4,247,454 | 1/1981 | Af Ekenstam et al. | 435/13 X |
| 4,508,644 | 4/1985 | Heber et al. | |
| 4,594,326 | 6/1986 | Wade | 436/501 |
| 4,672,030 | 6/1987 | Witt | 435/13 |
| 4,851,336 | 7/1989 | Yin | 435/13 |

FOREIGN PATENT DOCUMENTS 0014039  8/1980  European Pat. Off. .
0049877  4/1982  European Pat. Off. .

OTHER PUBLICATIONS

Becker et al, Clin. Chem., vol. 30, No. 4, pp. 524-528, 1984.
Van Wijk et al. Clin. Chem, vol. 26, No. 7, pp. 885-890, 1980.
Yamada et al, Thrombosis Research, vol. 15, pp. 351-358, 1979.
"Thrombosis and Thrombin", Biology and Pathology of Platelet-Vessel Wall Interactions, Chapter 13, 1986, By. H. Hemker et al., pp. 219-226.
"The Generation of Thrombin in Whole Plasma", Verhandelingen Van De Koninklijke Academie Voor Geneeskunde Van Belgie, No. 5, 1985, By H. Hemker et al., pp. 321-339.
"The Search for Antithrombotic Therapy", Publikationen der Jung-Stiftung Fur Wissenschaft und Forschung, vol. 1, Chapter IV, By H. Hemker, pp. 66-72.
"A Standard for Low Molecular Weight Heparin?", Haemostasis, 1989, By H. Hemker, pp. 1-4.
"The Mode of Action of Heparin in Plasma", Thrombosis and Haemostasis, vol. 60, No. 3, 1988, By S. Beguin et al., pp. 457-462.
"The Mode of Action of Heparin in Plasma", Thrombosis and Haemostasis 1987, By H. Hemker, pp. 17-36.
"The Mode of Action of Low Molecular Weight Heparin Preparation (PK10169) and Two of its Major Components on Thrombin Generation in Plasma", Thrombosis and Haemostasis, vol. 61, No. 1, 1989, By S. Beguin et al., pp. 30-34.

Primary Examiner—Robert J. Hill, Jr.
Attorney, Agent, or Firm—Young & Thompson

[57] ABSTRACT

A method for determining the endogenous thrombin potential (ETP), which shows how much and for what length of time thrombin has been active in a sample of clotting blood or plasma. The ETP can be used for determining the effectiveness of treatment with antithrombotics of any type. Thus, the ETP determination comprises adding to a sample a thrombin substrate, an activator of thrombin formation, a preparation of proteaseinhibitor and if desired a pharmaceutical for analysis. The thrombin substrate is preferably selected to not completely consume the amount of thrombin generated in the sample, to have a rate of conversion of the substrate which is proportional to the amount of thrombin present and to have a measurable conversion product resulting from the conversion by thrombin. Determination of the amount of conversion product leads to determination of the ETP. The choice of activator determines whether the effect is measured on the intrinsic or extrinsic clotting system, making it possible to determine the effect of the pharmaceutical, which is being analyzed, on various parts of the clotting mechanism.

33 Claims, 2 Drawing Sheets

METHOD FOR DETERMINING THE ENDOGENOUS THROMBIN POTENTIAL OF PLASMA AND BLOOD

FIELD OF THE INVENTION

The present invention relates to a method for determining the amount of thrombin which has been present in a sample of plasma or blood, and also a kit for use in said method.

BACKGROUND OF THE INVENTION

Deviations in the clotting system may result in thrombosis and haemophilia. Thrombosis results in diseases such as myocardial infarction and attacks and is a complication which frequently occurs in surgery and internal diseases. The formation of thrombin occupies a central role in haemostasis and thrombosis. The most efficient drugs for preventing thrombosis and for the treatment thereof are those agents which have the effect that less thrombin appears in clotting blood. Without going into great detail, it is first necessary to state the outlines of the formation and deactivation of thrombin. When clotting occurs in blood, in plasma which is rich in blood platelets (PRP) or in plasma which contains few blood platelets (LPP) the enzyme prothrombinase is produced therein. This can be produced in various ways, namely by the intrinsic reaction route via activation of the contact factors and factor IX or by the extrinsic reaction route via the activation of factor VII by tissue thromboplastin. Factors VIII and V, which are activated by the first traces of thrombin which appear, are essential cofactors. Factor IXa, together with factor VIIIa and clotting-promoting phospholipids, form a complex which activates factor X. Said factor Xa, together with factor Va and phospholipids, forms prothrombinase, the complex which converts prothrombin (factor II) into thrombin (factor IIa).

Pathology teaches that the deactivation of thrombin is extremely important in preventing thrombosis. No living individuals are known who have less than half the normal amount of ATIII, probably because the absence of it is lethal. People having a hereditary condition which results in them having approximately half the normal amount of ATIII suffer from serious thrombotic disease. To reduce the thrombin, provision can be made for it to be produced to a lesser extent or more slowly by inhibiting the prothrombinase or by reducing the prothrombin concentration in the blood or plasma. This method is used in oral anticlotting, in which the synthesis of plasma proteins in the liver, which are required for the clotting process (the clotting factors) is inhibited by administering vitamin K antagonists. Both prothrombin- and prothrombinase-forming factors are sensitive to vitamin K. The amounts of enzyme and substrate are reduced and the rate of formation of thrombin is reduced. A second way of reducing the amount of thrombin in the blood or plasma is more rapid deactivation of thrombin.

As soon as thrombin appears in the plasma, a number of processes for deactivating it occur, which processes thrombin combines to form inert complexes with its natural inhibitors such as antithrombin III (ATIII), heparin cofactor II (HCII), $\alpha_2$-macroglobulin($\alpha_2$-M) and others. Various pharmaceuticals such as, inter alia, the various types of heparin or dermatan sulphate, heparin sulphate, pentosan polysulphate, lactobionic acid or acidic mucopolysaccharides obtained, for example, from *Stichopus japonicus* (SJAMP) increase the effect of ATIII and/or HCII, which results in more rapid deactivation of thrombin occurring. It is also possible to administer substances which act directly on thrombin without an inhibiting plasma protein also being necessary; such as hirudine (Stone and Hofsteenge, Biochemistry, 25, 4622 (1986)) and synthetic direct thrombin inhibitors such as MD850 (Kumada and Abiko, Throb. Res. 24, 285 (1981)).

The rate of deactivation is proportional to the amount of thrombin present. As long as the rate of thrombin formation exceeds that of the deactivation, the concentration of thrombin in the plasma increases. When the prothrombin is exhausted, the rate of thrombin formation decreases, the deactivation soon acquires the upper hand and ultimately no active thrombin is left (FIG. 1, curve A). The area under the curve indicates how much thrombin has been active in the clotting blood or plasma and for what length of time. This thrombin concentration/time integral is termed the thrombin potential. The potential may decrease (FIG. 1, curve B) if less thrombin is present during coagulation and/or thrombin is present for a shorter time. During treatment with the antithrombotics described above, the thrombin formation curve alters in one or more of the following respects (FIG. 1, curves A and B). It begins later, i.e. the latency time before explosive formation of thrombin occurs is longer, the peak is lower and the decrease is more rapid, with the result that the thrombin present is deactivated earlier. It has been shown that both a reduced formation (in the case of oral anticlotting) and a more rapid decrease (in the case of treatment with heparin) are effective antithrombotic treatments. Both result in a smaller area under the thrombin formation curve. Said area, the time/concentration integral or the endogenous thrombin potential ETP, is therefore capable of being a good measure in determining the effectiveness of treatment with antithrombotics. The present method serves to determine a number (hereinafter to be termed the endogenous thrombin potential ETP) which shows how much thrombin has been active in the clotting blood (blood plasma) and for what length of time.

As far as is known, there is no method of measuring the ETP or a variable quantity of comparable importance. There is a method of calculating the ETP from a thrombin formation curve, which is involved and time-consuming, and there are a plurality of tests for tracking the effect of various types of treatment with antithrombotics with more or less specificity. Said tests are clearly different from, and/or more cumbersome than, the present method and are briefly described below.

THE KNOWN PRIOR ART a) Determination of the clotting time with the aid of tissue thromboplastin (prothrombin time PT). This method is sensitive to oral anticlotting, but insensitive to heparin.

b) Determination of the clotting time with the aid of contact activators and phospholipids (activated partial thromboplastin time (aPTT) (Teien, Abildagard, Hook and Lindahl, Thromb. Res. 11, 107 (1977); Bain, Forster and Sleigh, Am. Soc. Clin. Pathol. 35, 668 (1980)). This method is sensitive to heparin and oral anticlotting but not, or virtually not, to heparins having a low molecular weight or to dermatan sulphate. The Heptest is an aPTT test which, although it becomes more sensitive to heparins having a low molecular weight by adding isolated factor Xa, has a low sensitivity to other antithrombotics.

c) Measurement of the rate of disappearance of added thrombin (anti-IIa) (Handeland and Abildagard, Thromb. Res. 35, 627 (1984); Bartl, Dorsch, Lill and Ziegenhorn, Thromb. Hemostas. 42, 1446 (1980)). This method measures a nonphysiological parameter and is insensitive to heparins having low molecular weight. It is known that there are fundamental differences between the behaviour of thrombin which is added to blood (blood plasma) and thrombin which is formed in blood (blood plasma). Endogenous thrombin is less sensitive to ATIII (heparin) action (Thrombosis and Hemostasis, F. K. Schattauer, Verlagsgesellschaft GmbH (Stuttgart), 56, 9-17 (1986) and 61, 30-34 (1989)).

d) Measurement of the disappearance of added factor X (anti-Xa) (Teien, Lie and Abildagard, Thromb. Res. 8, 413 (1976)). In this, something is measured which correlates poorly with antithrombotic properties. This method is suitable only for heparins and gives essentially different results with in vivo equally active doses of unfractionated heparin, low-molecular-weight heparin and ultra-low-molecular-weight (P-type) heparin respectively. In addition, the effects of dermatan sulphate and other thrombotics cannot be determined singly or in conjunction with heparin cofactor II by this anti-Xa method.

e) Titration of the heparin effect with polybrene (Hoffmann and Meulendijk, Clin. Chim. Acta 87, 417 (1978)). This method is very labour-intensive and is suitable only for heparins.

f) A modified aPTT which is dependent on heparin by adding factor Xa. (Denson and Bonnar, Thromb. Diathes. Haemorrh. 30, 471 (1973); Yin, Wessler and Butler, J. Lab. Clin. Ned. 81, 298 (1973); Yin, Thromb. Diathes. Haemorrh. 33, 393 (1975)). This method is suitable only for heparins having a low molecular weight. The most important point is that none of the methods measures the amount of thrombin which is produced in the plasma and disappears again. Secondary effects are measured, primarily the effect of the pharmaceuticals on the activation of the clotting mechanism, which are caused by small amounts of thrombin which are produced during the latency time of a clotting time determination (a, b and f).

g) Hemker, Beguin et al. have invented two methods of investigating the effect of antithrombotics on prothrombinase formation and deactivation in clotting plasma. An indirect method in which the activity of prothrombinase was calculated from the formation of thrombin-like amidolytic activity and a direct measurement of residual prothrombin levels. The indirect method is more precise and more rapid (Hemker H. C., Willems G. and Beguin S., Thrombosis and Haemostasis 56, 9-17 (1986)). This method was used, inter alia, to investigate the effect of the antithrombotic heparin in plasma (Beguin S., Lindhout T. and Hemker H. C., Thrombosis and Haemostasis 56, 9-17 (1989)). To a good approximation, the degradation of thrombin in the presence of heparin can be described as the sum of two pseudo first order reactions, one which completely deactivates thrombin (complex formation by ATIII and thrombin inhibitors of less importance) and the other which yields a product having an amidolytic activity ($\alpha_2$-macroglobulin/thrombin complex). It was possible to calculate the variation of prothrombinase activity with time in the presence or absence of heparin. These results are compared with the rates of consumption of prothrombin such as those which were measured directly with the aid of staphylocoagulase. This method comprises calculating differences between large values for which the standard deviation of the resultant rate at which prothrombin disappears was calculated to be between 9 and 15%. The values calculated by the indirect method agree well with those determined via the direct method, so that the mathematical approach gives an acceptable picture of the rate at which prothrombin is activated in the presence and absence of heparin. Data analysis yielded a first order thrombin inactivation rate constant for $\alpha_2$-macroglobulin of $0.232\pm0.004$ $min^{-1}$, which is independent of the heparin concentrations. It was also possible to plot the rate constant for the inhibition of thrombin formed in plasma, which constant is dependent on antithrombin III, as a function of the heparin concentration.

BRIEF DESCRIPTION OF THE INVENTION

The present invention provides a method of the type described in the preamble. This method is characterized in that the potential of endogenous thrombin is determined. The invention furthermore relates to a kit for carrying out the abovementioned determination. The use of the present method facilitates and accelerates the determination of the ETP, with the result that it can be used for determining the effect of antithrombotic treatment in the clinic and in experimental animals. The present method is not comparable in any way with existing methods. Hitherto no single method has been known which can be used universally for all the antithrombotics and which provides a measure of the amount of active thrombin which is present in the plasma during the clotting process.

The invention yields a very sensitive, reproducible and easy test for determining the time integral of the thrombin concentration in clotting blood, i.e. of the area under the thrombin formation curve, defined here as the endogenous thrombin potential or ETP. The method is based on adding the reaction mixture to be tested to a solution containing a clotting process activator, a source of $Ca^{++}$ ions, a preparation of a natural antithrombotic and a thrombin substrate. The reaction mixture is either a sample of the blood, platelet-rich plasma, low-platelet plasma or defibrinated plasma of a patient (or experimental animal) who (which) is undergoing an antithrombotic treatment with a pharmaceutical (possibly, a plurality of pharmaceuticals) or normal blood or plasma to which a known amount of the pharmaceutical concerned has been added. The natural antithrombotic preparation may contain either ATIII (antithrombin III), or HCII (heparin cofactor II) or both. The presence of additional ATIII and/or HCII serves a plurality of purposes. Thrombin is preferred for these inhibitors to other antithrombotics such as, for example, $\alpha_2$-macroglobulin ($\alpha_2$-M) (Thrombosis and Haemostasis 1987, edited by M. Verstraten, J. Vermeylen, H. v. Lynen and J. Arnout, International Society on Thrombosis and Haemostasis, Leuven University Press, Leuven 1987, chapter 2, page 23) in order to minimize the side reactions. As a result, the method also becomes virtually independent of the ATIII and/or HCII content of the sample. In addition to this, the test can be made specifically sensitive to a particular type of drug by choosing one of the two inhibitors. Heparin, for example, catalyses the reaction of thrombin with ATIII and dermatan sulphate catalyses that of thrombin with HCII. This specificity may increase still further as a result of the (immuno)reduction of the other inhibitor. The mixture containing the sample to be tested is incubated for a certain time under certain conditions. Then the amount of thrombin substrate is measured directly or, in the case of opaque solutions, the reaction is stopped by adding a thrombin inhibitor and the mixture is treated, for example centrifuged, in order to make possible the determination of the amount of the product formed or the determination of the amount of substrate which has disappeared. Possible thrombin inhibitors contain benzamidine (this substance is used in the example), hirudin or N-(2-naphthylsulphonylglycyl)-D.L-amidine-phenylalaninepiperidine. HCl ($\alpha$-NAPAP). In optically clear solutions, it is also possible to track the amount of product formed spectrophotometrically. This last possibility is of particular importance because the first derivative of the curve obtained represents the variation in thrombin formation in the sample.

DETAILED DESCRIPTION OF THE INVENTION

Figure 1:
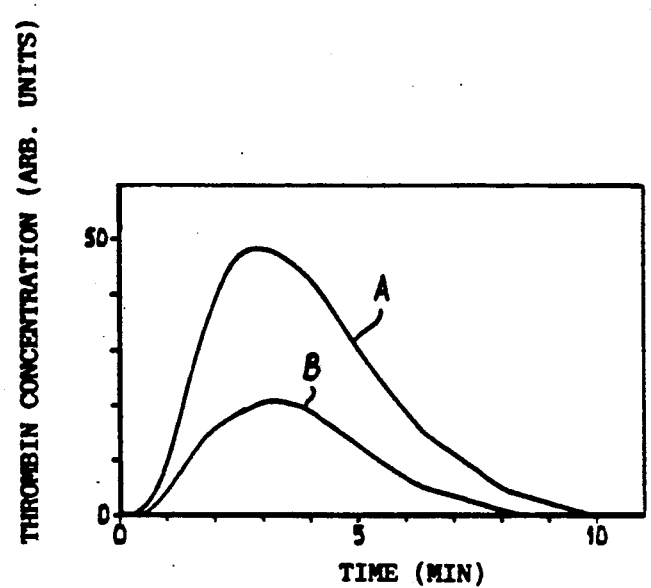
FIG. 1 is a graph showing thrombin generation curves.

More particularly, the accompanying figures of drawings show the following:

FIG. 1:
(1) Thrombin concentration (arbitrary units)
(2) Thrombin generation curves
(3) Time (min)
(4) The thrombin generation curve Curve A gives the normal variation of the thrombin generation curve after the clotting has been started at t=0. Curve B gives the same curve in the presence of an antithrombotic.

Figure 2:
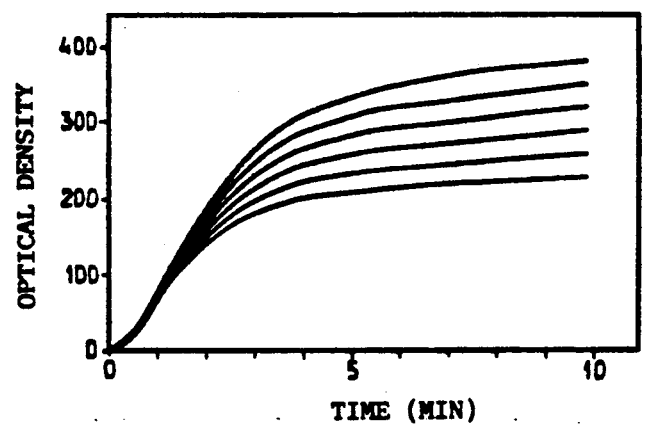
FIG. 2 is a graph showing substrate consumption during coagulation.

FIG. 2:
(1) Substrate consumption during clotting
(2) Optical density (mOD)
(3) Time (min)
(4) Thrombin potential determination Recording of the O.D. variation in the test of Example 1. From top to bottom: curves obtained in the presence of increasing heparin concentrations.

Figure 3:
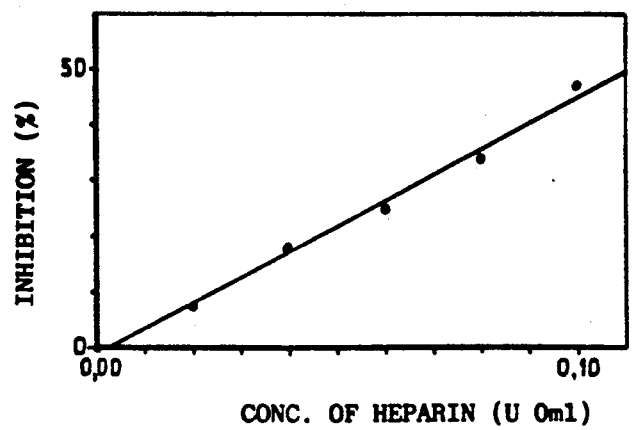
FIG. 3 is a graph of the inhibition of substrate consumption.

FIG. 3:
(1) Inhibition of substrate consumption
(2) Inhibition (%)
(3) Heparin concentration (UDml)
(4) ETP and heparin concentration The inhibition of the substrate conversion determined in FIG. 2 as a function of the amount of heparin added.

Figure 4:
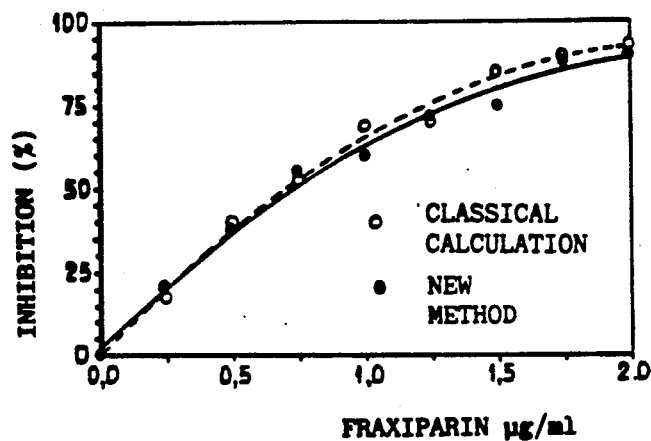
FIG. 4 is a graph of thrombin potential.

FIG. 4:
(1) Thrombin potential
(2) Inhibition (%)
(3) Fraxiparine, $\mu$g/ml
(4) Conventional calculation
(5) New method (6) Comparison of old and new method Data from Example 2. The ETP was calculated from thrombin generation curves obtained in the conventional way and by the new method in the presence of a series of concentrations of low-molecular-weight heparin (Fraxiparine).

Figure 5:
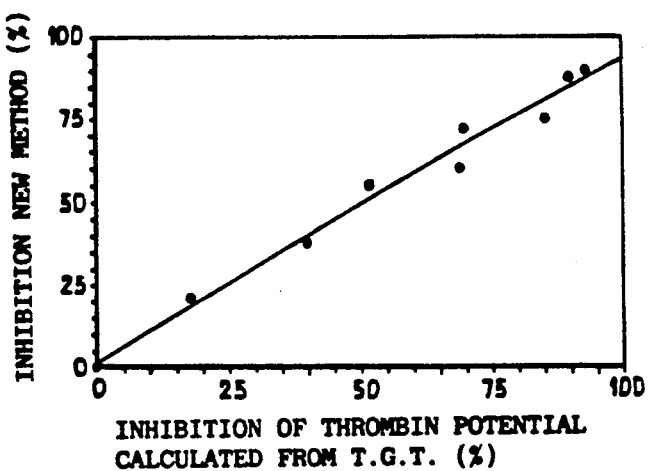
FIG. 5 is a graph of inhibition of thrombin potential by fraxiparine.

FIG. 5:
(1) Thrombin potential inhibition due to Fraxiparine
(2) New method inhibition (%)
(3) Inhibition of thrombin potential calculated from T.G.T. (%)
(4) Comparison of old and new method Here the data from FIG. 4 obtained by the two methods are compared with each other.

Figure 6:
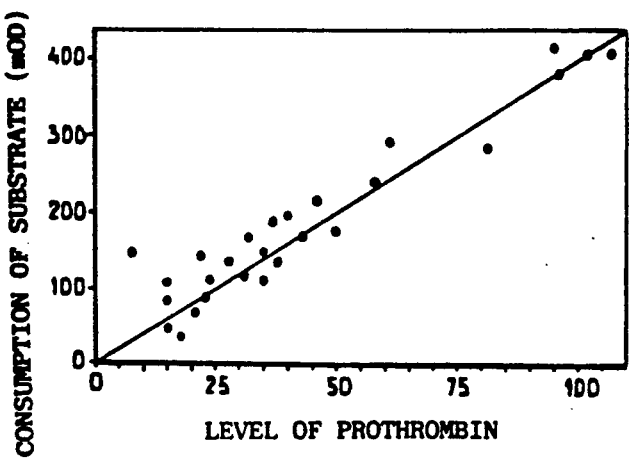
FIG. 6 is a graph of endogenous thrombin potential and oral anticoagulation.

FIG. 6:
(1) Endogenous thrombin potential and orale anticlotting
(2) Substrate consumption (mOD)
(3) Prothrombin level
(4) E.T.P. and oral anticlotting The ETP determined in Example 3 is compared with the prothrombin content of the plasma taken from the same patient.

In the example described below, Experiment 1, the variation in the amidolytic activity in plasma is measured spectrophotometrically at 405 nm on the basis of the development of p-nitroaniline. In Experiment 2, measurement is carried out after a certain reaction time has elapsed. In Experiment 3, the reaction is stopped after a certain time by adding a thrombin inhibitor, after which the reaction mixture is treated (centrifuged) in order to be able to measure the reaction product.

The reactions below illustrate the present method further;

1) clotting factors (V-XII) activator prothrombinate
2) prothrombin prothrombinase thrombin
3) thrombin + antithrombotics → inactive complexes
4) substrate thrombin signal molecule Reactions 2 and 3 are irreversible, with the result that thrombin is only temporarily present in the reaction mixture. While thrombin is present, it participates in reaction 4, with the result that the degree of conversion of the substrate indicates the time for which, and the amount to which, thrombin has catalysed this reaction. It is essential that the amount of substrate is not exhausted before the thrombin disappears. In the ideal case, the reaction rate should be proportional to the concentration of thrombin at any instant in time. This can be achieved in practice if, at the beginning of the reaction, the concentration of substrate is several times greater than the $K_m$ of said substrate for thrombin and if a modest portion of the substrate is consumed, with the result that the final concentration remains appreciably higher than the $K_m$. The substrate must be converted by thrombin, but not so rapidly that impossibly high concentrations of the substrate would have to be added to the test in order to prevent the substrate becoming depleted. For this reason, the very specific substrate S2238 (HD-Phe-Pip-Arg-pNa) is much less suitable than the substrates used in the examples.

A substrate is as a rule composed of an oligopeptide to which a "leaving group" is coupled (the leaving group is the group which splits off after reaction of the substrate with thrombin). The oligopeptide generally determines the specificity and the "leaving group" acquires measurable properties on splitting off. An example of another substrate is the methyl ester of tosylarginine. The arginine determines that thrombin has affinity for this substrate. The release of H+ ions during the splitting may be used as a signal. There are also substrates which do not release a chromophoric group such as p-nitroaniline but a fluorescent group. For each substrate, this is a question of searching skillfully. If there is a rectilinear proportionality between the rate of conversion of the substrate and the amount of thrombin present, there will also be rectilinear proportionality between the amount of substrate split and the area under the curves in FIG. 1, that is to say the thrombin potential. If there is no rectilinear proportionality between the rate of conversion of the substrate and the amount of thrombin present, the proportionality between the amount of substrate split and the thrombin potential will be of a more involved nature. The amount of thrombin which has been present in the plasma during the test is unknown but can be calculated from the amount of product formed (p-nitroaniline in the examples) because the kinetic parameters $k_c$at and $K_m$ of the action of thrombin on the substrate are known. The thrombin time curve can be obtained as described in Hemker, Beguin and Willems (Thrombosis and Haemostasis 56, 9 (1986)). The essence of the present method is, however, that said curve is not determined at all. FIG. 1 is given only for the purpose of the theoretical basis. The present method is used to determine the area under the thrombin/time curve (of which, however, no mathematically analytical expression can be given). The experimental curves from FIG. 2 are the integral of those in FIG. 1, since the rate of product formation is proportional to the amount of thrombin. For this reason, the final level of the experimental curves is equal to the area under the thrombin/time curve, that is to say to the thrombin potential. In practice, for use with patients and in pharmacological research, this final level will generally be the only one which is determined. Owing to the persistent, albeit low, activity of the complex of thrombin with $\alpha_2$-microglobulin, it may be necessary to measure the final level after a fixed reaction time. In the present method, the thrombin potential is determined directly. In all cases there will be a relationship between the amount of split substrate and the amount of pharmaceutical present (for example heparin or another drug). This is precisely the relationship which can be determined experimentally by this method.

The choice of activator determines whether the effect is measured on the intrinsic or extrinsic clotting system. If thromboplastin is used, the combined effect of the presence of the drug on the formation of prothrombinase (if this occurs) and the disappearance of thrombin is measured. If the intrinsic route is activated by a contact activator, for example kaolin, with or without phospholipids, the combined effect is again measured, but the prothrombinase formation will now be dependent on the feedback activation of thrombin on blood-clotting factor VIII, which occurs only in the intrinsic route. Targeted choice of the activating agent makes it possible for the effect of the drug on various parts of the clotting mechanism to be tested. Activation by small amounts of thromboplastin from tissue is of particular interest because this probably gives the best approximation of the physiological situation. If snake poison (for example *Oxyuranus scutellatus* poison) is used, a synthetic prothrombin activator which is insensitive to the inhibiting action of ATIII and HCII, and other poisons which are insensitive to the action of heparin, it is possible to investigate whether the reduction in the thrombin potential is caused solely by accelerated degradation of thrombin or also by inhibition of the physiological prothrombinase. Physiological prothrombin activator is sometimes sensitive and sometimes not. If inhibition of the physiological prothrombinase occurs, a higher thrombin potential will be measured with snake poison than under physiological conditions.

The present invention also relates both to equipment for routinely carrying out the determination of the thrombin potential according to the above method and also to supplying a source of test components in bulk quantity for facilitating the operation of automated appliances which can process large amounts of test samples. The test equipment comprises a container containing the following reactants (and, if desired, an instruction):

one or more substances which start the thrombin formation, including at least $Ca^{++}$ ions (with, in addition, for example a thromboplastin, a contact activator or a snake poison), a thrombin inhibitor preparation which is sensitive to the pharmaceutical to be tested (antithrombin III and/or heparin cofactor II), a suitable thrombin substrate (for example S2222 or $CH_3OCO$-Gly-Pro-Arg-pNA.AcOH), any possible preservatives.

To increase the shelf life, the solution may possibly be freeze-dried and dissolved in a specified amount of water shortly before use. Containers can be made which are suitable for a certain number of determinations, but the desired amount of solution can also be freeze-dried in individual tubes or cuvettes to which it is only necessary for water and/or a sample to be added.

After a specified incubation time at a specified temperature, the measurement is carried out or a thrombin inhibitor (for example, benzamidine, hirudin or $\alpha$-NAPAP) is added to stop the reaction. The reaction then has, possibly, to undergo a treatment (centrifugation, precipitation or something similar) which makes it possible to measure the amount of product formed. The inhibiting liquid is added to the kit in a separate container and is used if the sample to be tested is opaque and the amount of thrombin substrate cannot consequently be read off directly.

EXAMPLES

Reagents:

Buffer: 0.05M Tris HCl, pH 7.35, 0.1M NaCl, 0.5% egg albumin.

Blood: Blood obtained by venepuncture of normal or anticlotting test persons/animals. 9 parts of blood were collected to 1 part of 0.13 M trisodium citrate.

Platelet-rich plasma: Colourless blood supernatant after centrifugation at room temperature and at 3000 g.

Low-platelet plasma: the blood was centrifuged twice for 15 min. at 3000 g and 15° C. A third centrifugation was carried out for 60 min. at 2300 g and 4° C.

Defibrinated plasma: Low-platelet plasma was incubated with 0.1 part of reptilase for 10 min. at 37° C. and was then placed on ice for 10 minutes. The fibrin formed was removed by means of centrifugation for 10 min. at 5000 g and 0° C. or by winding it around a spatula.

Thromboplastin; This was prepared in accordance with Owren and Aas, Scand. J. Clin. Lab. Invest. 3, 201, (1951). Before use it was diluted 40 times.

Antithrombin III: This was isolated in accordance with Thaler and Schmer, Br. J. Haemat. 31, 233 (1975).

Other reagents: these were obtained commercially.

Equipment: Pipettes, tubes etc. A water bath at 37° C. A spectrometer which is capable of recording the optical density at 405 nm and which has a cuvette holder whose temperature can be regulated.

EXAMPLE 1

As far as necessary, all the reagents are dissolved in the buffer already described.

A 400 microliter solution was prepared which contained:

40 μl of S2222 (N-benzoyl-L-isoleucyl-L-glutamylg-lycyl-L-arginine-p-nitroanilide HCl), conc: L 0.4 mm,
thromboplastin: 1.25%,
$CaCl_2$: 7.5 mM,
ATIII: 2.5 μmol/l.

The solution is preheated for at least 2 minutes in the water bath. The reaction is started with 200 μl of defibrinated plasma containing various amounts of heparin. The pattern of the increase in optical density at 405 nm is tracked. The spectrophotometric results are given in FIG. 2. It can be seen that the final level of the amount of p-nitroaniline produced decreases in proportion to the amount of heparin which was in the plasma.

The curves of FIG. 2 are of particular importance because the first derivatives represent the analogue of the classical thrombin formation test. This implies that they can be used to determine the thrombin formation curve and to measure both the ETP and the instant in time at which a particular low level (for example 10 mM) of thrombin is formed. In this way, the latency time of the system corresponding to the classical clotting time can be determined. FIG. 3 shows that there is a linear relationship between the percentage inhibition of the final level of p-nitroaniline and the amount of heparin which was present in the sample.

In the present example, the plasma was defibrinated by adding reptilase to obtain undisturbed spectrophotometric data. In practice, this is unnecessary. Low-platelet plasma (LPP), platelet-rich plasma (PRP) or whole blood can be used but the mixture then has to be centrifuged before measuring.

In the present experiment, normal plasma to which heparin had been added was used. In practice, heparin concentration series of this type can be used to obtain standard curves. If blood or plasma of patients who have been treated with heparin is tested, the figure obtained from the sample taken from the patient can be compared with the standard curve. In this way, the amount of heparin which is equivalent to that present in the sample taken from the patient can be found. A similar procedure can be adopted using other pharmaceuticals.

It should be pointed out that, although it is known as being a specific substrate for factor Xa, S2222 is used as thrombin substrate in this experiment. This is possible because the concentration of thrombin is so much higher than that of factor Xa, with the result that the activity of the latter makes hardly any contribution to the total substrate conversion measured.

EXAMPLE 2

The following are added to the buffer described above:

0.75 nM AcGPRpNA ($CH_3OCO$-Gly-Pro-Arg-p-nitroanilide.HCl)
2% thromboplastin,
7.5 mM $CaCl_2$,
3 mM antithrombin III.

At instant in time 0, 400 microliters of defibrinated plasma are added to 400 microliters of this mixture. The plasma added contains various concentrations of a heparin having a low molecular weight (Fraxiparine). After 6 minutes, the optical density is measured at 405 nm.

The ■OD per minute at that instant in time is also determined and 6 times its value is subtracted from the OD at t=6 min. In this way, the change in OD is measured independently of the persistent amidolytic activity after the thrombin formation process has started. The percentage inhibition of the value obtained in this way and the amount of Fraxiparine added is shown in FIG. 4. In the same figure, the inhibition by the same concentrations of Fraxiparine is provided by the area under the thrombin/time curve, demonstrating that the figure obtained according to the invention is in fact directly proportional to the thrombin potential. In FIG. 5, the values obtained according to the old and the present method are directly compared.

FIG. 3

The same solution is used as in Experiment 2. 400 microliters of blood obtained by venepuncture of four healthy volunteers and 24 patients who have been under a prolonged anticlotting treatment are added to 400 microliters of this solution. After 6 minutes, the reaction is stopped by adding 400 microliters of a solution of benzamidine (10 mM) in 0.15M NaCl. The samples are centrifuged and the increase in the optical density (OD) at 405 nm is determined. This increase is determined by comparing the value obtained in a control test carried out with the same plasma which has undergone an identical treatment with the exception that a solution not containing chromogenic substrate is added at instant in time t=0. The number read off in this way is used as a direct measure of the thrombin potential. In FIG. 6, the results obtained are compared with the thrombin content of the same samples. Since the prothrombin content of these patients may be regarded as a measure of the effect of the anticlotting treatment, this test demonstrates that the thrombin potential measured according to the present method is a measure of the intensity of the anticlotting treatment.

We claim:

1. A method for determining the amount of thrombin present in a sample of either clotting blood or plasma through determination of the potential of endogenous thrombin comprising adding a thrombin formation activator to the sample together with a thrombin substrate, wherein the amount and also the kinetic properties of said thrombin substrate are chosen such that the amount of thrombin generated in the sample cannot completely consume said thrombin substrate, thereby to produce a conversion product, measuring the amount of said conversion product thus produced, and from this determining the endogenous thrombin potential in the sample.

2. A method according to claim 1, wherein a protease inhibitor preparation is added to the sample together with the thrombin formation activator and the thrombin substrate.

3. A method according to claim 2, wherein the protease inhibitor preparation comprises at least one of AT III and HCII.

4. A method according to claim 3, wherein the protease inhibitor originates from an animal.

5. A method according to claim 1, wherein a pharmaceutical to be tested for its influence on clotting of the sample is added to the sample together with the thrombin formation activator and the thrombin substrate.

6. A method according to claim 5, wherein the pharmaceutical to be tested is an antithrombotic.

7. A method according to claim 6, wherein the antithrombotic is heparin.

8. A method according to claim 6, wherein the antithrombotic is dermatan sulphate.

9. A method according to claim 1, wherein the inhibition of thrombin formation in the sample is determined.

10. A method according to claim 1, wherein the thrombin substrate is selected so tat the rate of conversion of said thrombin substrate in the sample is proportional to the amount of thrombin present.

11. A method according to claim 1, wherein the amount of converted thrombin substrate in the sample is directly proportional to the thrombin potential.

12. A method according to claim 1, wherein the amount of converted thrombin substrate in the sample is not directly proportional to the thrombin potential.

13. A method according to claim 1, wherein the thrombin substrate is S2222 (N-benzoyl-L-isoleucyl-L-glutamyl-glycyl-L-arginine-p-nitroanilide.HCl).

14. A method according to claim 1, wherein the thrombin substrate is AcGPR$_p$NA (CH$_3$OCO-Gly-Pro-Arg-p-nitro-anilide.HCl).

15. A method according to claim 1, wherein the thrombin substrate is composed of a portion with specificity for thrombin and a "leaving group" that is released when said thrombin substrate reacts with thrombin.

16. A method according to claim 15, wherein the thrombin substrate comprises an oligopeptide as the portion with specificity for thrombin.

17. A method according to claim 16, wherein the thrombin substrate comprises an arginine-containing oligopeptide.

18. A method according to claim 17, wherein the thrombin substrate comprises a methylester of tosylarginine.

19. A method according to claim 15, wherein the leaving group has measurable properties.

20. A method according to claim 15, wherein the leaving group comprises a fluorescent group.

21. A method according to claim 15, wherein the leaving group comprises a chromophoric group.

22. A method according to claim 15, wherein the leaving group comprises H$^+$ ions.

23. A method according to claim 1, wherein a thrombin inhibitor is added to an opaque sample.

24. A method according to claim 1, wherein a thrombin inhibitor selected from the group consisting of benzamidine, hirudine and n-(2-naphtylsulphonylglycyl)-D,L-amidinephenylalaninepiperidine.HCl ($\alpha$-NAPAP) is added to the sample, and then ETP is determined.

25. A method according to claim 1, wherein the sample is defibrinated.

26. A method according to claim 1, wherein the thrombin formation activator comprises Ca$^{2+}$ ions.

27. A method according to claim 1, wherein the thrombin formation activator is insensitive to AT III.

28. A method according to claim 1, wherein the thrombin formation activator is insensitive to HC II.

29. A method according to claim 1, wherein the thrombin formation activator is the poison *Oxyuranus scutellatis*.

30. A method according to claim 1, wherein the thrombin formation activator is a contact activator.

31. A method according to claim 1, wherein the thrombin formation activator is thromboplastin.

32. A method according to claim 1, wherein the sample is blood or plasma from a patient or experimental animal undergoing antithrombotic treatment with a pharmaceutical.

33. A method according to claim 1, wherein the sample is normal blood or normal plasma to which a known amount of a pharmaceutical to be tested has been added.

* * * * *

UNITED STATES PATENT AND TRADEMARK OFFICE
CERTIFICATE OF CORRECTION

PATENT NO. : 5,192,689

DATED : March 9, 1993

INVENTOR(S) : Henrik Coenraad HEMKER et al.

It is certified that error appears in the above—identified patent and that said Letters Patent is hereby corrected as shown below:

On the title page, in the Abstract, line 11, change "not completely consume" to --not be completely consumed by--.

Column 1, line 8, after "present" insert --during coagulation--; line 61, cancel "for"; before "which" insert --in--.

Column 2, line 61, change "Abildagard," to --Abildgaard,--.

Column 3, line 4, change "Abildagard," to --Abildgaard,--; line 18, change "Abildagard," to --Abildgaard,--.

Column 4, line 43, change "$Ca^+{+}$" to --$Ca^{++}$--; lines 43-44, change "antithrombotic" to --anti-thrombin--; line 51, change "antithrombotic" to --antithrombin--; line 55, change "Thrombin is" to --AT-III and HC-II are--; line 56, change "antithrombotics" to --antithrombins--.

Column 5, line 44, change "cancel "variation of the".

Column 6, line 35, change "(V-XII) activator prothrombinate" to --$(V-XII)^{activator}$ prothrombinase--; line 36, change "prothrombin prothrombinase" to --$prothrombin^{prothrombinase}$--.

Column 7, line 19, change "$k_c at$" to --$k_{cat}$--; line 64, cancel "synthetic".

Column 8, line 51, change "anticlotting" to --anticoagulated--.

UNITED STATES PATENT AND TRADEMARK OFFICE
CERTIFICATE OF CORRECTION

PATENT NO. : 5,192,689
DATED : March 9, 1993
INVENTOR(S) : Henrik Coenraad HEMKER et al.

It is certified that error appears in the above—identified patent and that said Letters Patent is hereby corrected as shown below:

Column 9, line 58, cancel "so".

Column 10, line 8, change "∎OD" to --increase of OD--; line 23, change "FIG. 3" to --EXAMPLE 3--; line 28, change "anticlotting" to --oral anticoagulation--.

Column 11, line 15 (claim 10, line 2), change "tat" to --that--.

Signed and Sealed this

Fourth Day of October, 1994

BRUCE LEHMAN

*Attest:*

*Attesting Officer*       *Commissioner of Patents and Trademarks*